United States Patent [19]

Reed et al.

[11] Patent Number: 5,492,535
[45] Date of Patent: Feb. 20, 1996

[54] HAND-POWERED PUMPING APPARATUS FOR PERFUSION AND OTHER FLUID CATHETERIZATION PROCEDURES

[75] Inventors: Phillip G. Reed, Coconut Creek, Fla.; Andrea Slater, Somerville, N.J.

[73] Assignee: Cordis Corporation, Miami Lakes, Fla.

[21] Appl. No.: 223,869

[22] Filed: Apr. 6, 1994

[51] Int. Cl.⁶ .............................. A61M 1/00; F04B 11/00
[52] U.S. Cl. .......................... 604/152; 604/151; 417/539; 417/437
[58] Field of Search .................................. 604/152, 151, 604/131; 417/315, 437, 531, 539

[56] References Cited

U.S. PATENT DOCUMENTS

| | | | |
|---|---|---|---|
| 380,509 | 4/1888 | North | 417/539 |
| 805,530 | 11/1905 | Davis | 417/539 |
| 1,267,088 | 5/1918 | Lane | 417/539 |
| 2,393,175 | 1/1946 | Laskey . | |
| 2,545,315 | 3/1951 | Sproull . | |
| 2,896,621 | 7/1959 | Rodrigues . | |
| 3,099,260 | 7/1963 | Birtwell . | |
| 3,259,077 | 7/1966 | Wiley et al. . | |
| 3,447,479 | 6/1969 | Rosenberg . | |
| 3,818,907 | 6/1974 | Walton . | |
| 3,981,620 | 9/1976 | Abrahams | 417/539 |
| 4,490,331 | 12/1984 | Steg, Jr. . | |
| 4,634,430 | 1/1987 | Polaschegg | 604/141 |
| 4,867,742 | 9/1989 | Calderon | 604/28 |
| 4,985,014 | 1/1991 | Orejola | 600/16 |
| 5,066,282 | 11/1991 | Wijay et al. | 604/152 |
| 5,066,283 | 11/1991 | Skrabal . | |
| 5,325,867 | 7/1994 | Skrabal et al. | 604/152 |

OTHER PUBLICATIONS

Serial No. 186,667—Layer, "Pumping Apparatus for Perfusion and Other Fluid Catherization Procedures" filed Jan. 25, 1994.
Serial No. 223,867—Layer et al.—"Pumping Apparatus for Perfusion and Other Fluid Catherization Procedures" filed Apr. 19, 1994.

*Primary Examiner*—John G. Weiss
*Attorney, Agent, or Firm*—Lockwood, Alex, Fitzgibbon & Cummings

[57] ABSTRACT

A manually operated pumping apparatus which is particularly useful in catheterization procedures has two pumps supported in a housing in a parallel arrangement. The pumps are engaged by a rack and pinion actuating assembly which provides reciprocating linear movement to the two pumps during operation so that one pump performs a pumping stroke while the other pump simultaneously performs a suction stroke. The actuating assembly is driven by a drive assembly which converts rotation of a handle into linear motion usable by the rack and pinion members to drive the two pumps in their reciprocating pumping movements.

20 Claims, 3 Drawing Sheets

HAND-POWERED PUMPING APPARATUS FOR PERFUSION AND OTHER FLUID CATHETERIZATION PROCEDURES

BACKGROUND AND SUMMARY OF THE INVENTION

The present invention relates generally to equipment employed in the performance of perfusion catheterization procedures, and more particularly, to manually powered pumping apparatus which interconnects an aspiration catheter with a percutaneous transluminal coronary angioplasty (PTCA) catheter or the like to provide a constant, preselected flow of body fluids through the catheter.

Inflatable balloon catheters are commonly used in the treatment of coronary conditions by expanding blockages in arteries. These blockages constitute a narrowing of an artery and are referred to as a stenoses. In coronary procedures, and particularly in PTCA procedures, a guide catheter is inserted into a patient's artery and guided therethrough until the catheter distal tip is positioned in the artery near the stenosis. A dilation catheter which has an inflatable balloon affixed to its distal end is introduced along the guide catheter and advanced along the guide catheter until the balloon end is located at the stenosis. The balloon is then inflated to expand it against the artery and thereby compress the stenosis. This balloon expansion may remove all or most of the blockage.

Once the artery has been expanded, the balloon is deflated. The balloon and guide catheter are subsequently removed and blood again flows through the artery. Often, after expansion and removal of the balloon, the arterial wall may contract and assume part of or its original, restricted state. This contraction is referred to as restenosis. Restenosis is believed to be avoided if the balloon is inflated for longer inflation times. Ischemia, which is a local deficiency of oxygen caused by an obstruction in a blood vessels, may occur with longer balloon inflation times.

Perfusion catheters are used in association with coronary angioplasty, or balloon, catheters to avoid ischemia. Perfusion catheters are catheters which permit the continuous flow of blood through the blockage during the inflation of the balloon in the artery. Perfusion of blood through a balloon catheter is accomplished by providing a balloon having one or more passages, or lumens, which serve as passages extending through the balloon. These passages permit blood to flow through the blockage and through the balloon. In perfusion, a reliable pump is needed to pump blood continuously through the balloon passages. A specific flow rate through perfusion catheters, such as 60 cc per minute is desirable to avoid ischemia. Perfusion catheter lumens possess minute diameters which are approximately three mils (0.003 inch). External pumps used for perfusion must provide a continuous flowrate of blood at high pressures approaching 300 psi or so to continuously pump blood at flowrates of 60 cc per minute or so. External pumps are needed in order to maintain these high pumping pressures and therefore pump blood through small lumens of these catheters through the balloon inflation area, rather than rely upon the patient's heart to pump the blood. These external pumps preferably would draw blood from the patient by way of an aspiration catheter and circulate it back into the patient through the perfusion catheter past the distal end of the balloon.

External blood pumps are well-known and have been commonly used for regulating blood through coronary arteries during open-heart surgeries, but necessarily for perfusion procedures. Open-heart pumps may include a roller type pumping apparatus and generally have a low pressure output and, thus may not be able to supply a high pressure necessary to pump blood at a flowrate of 60 cc per minute through perfusion catheter lumens. Positive displacement pumps which use conventionally powered pistons may create pressure pulses during pumping which may result in pressure transients during pumping. Single-stroke pumps at best may only provide intermittent blood flow because every pumping stroke of the pump requires a suction stroke to refill the pump piston.

A need therefore exists for reliable perfusion pump for use in PCTA and other catheterization procedures which continuously and simultaneously pumps and withdraws blood from and into a patient through small diameter catheter lumens. It would be further desirable if such perfusion pumps utilized disposable components, such as syringes, as their pumping members, to avoid repeated sterilization of the pump.

Some external syringe pumps are described in the art, such as the one described in U.S. Pat. No. 3,447,479, issued Jun. 2, 1967. This patent describes a multiple syringe pump arrangement which performs alternating suction and pumping strokes. In this multiple syringe pump arrangement, four syringe pumps are spaced--apart on a base and their plunger located in the center of the base in contact with a motor-driven eccentric cam. Return springs must be used on these pump plungers to ensure the prompt return of the plungers to their original positions within the syringes. This mechanism is unduly complicated and the possibility exists that the springs and cam may not always reliably power the pumps through a complete suction and pumping cycle because of wear.

The present invention is directed to a manually operated external pumping apparatus for use in catheterization, and particularly perfusion catheterization which continuously and reliably both withdraws blood from a patient and reintroduces the blood back into the patient by simultaneously performing a pumping stroke in one syringe and a suction stroke in another syringe.

In accordance with one aspect of the present invention, a housing member is provided which supports two positive displacement pumps, each of the pumps having a plunger slidable within a pump chamber, the plunger of one pump being affixed to a driving rack member and the plunger of another pump being affixed to a driven rack member. Both rack members are engaged by a pinion gear and the driving rack member further engages a pump handle. When the handle is rotated, the driving rack moves linearly back and forth to impart first a pumping action and second a suction action in the pump affixed to the driving rack. The pinion gear rotates in response to the movements of the driving rack member and this rotation induces a reverse linear movement in the driven rack member, such that while the driving rack member and pump affixed thereto performs a suction stroke, the other pump performs a pumping stroke and vice-versa. The pumping apparatus thus provides a continuous flow of blood during its operation.

In another aspect of the present invention, two syringe pumps of the type having a plunger slidable within a barrel portion are supported within two channels of the housing 12. Each channel engages the barrel portion of its associated pump and restrains them from movement relative to the plunger portions. An actuating mechanism reciprocates both plungers of the two pumps in opposite directions such that at any given moment during operation of the apparatus, the actuating mechanism engages the plunger member of one pump in a pumping mode and the plunger member of the other syringe pump in a suction mode. The actuating mechanism includes a rack and pinion assembly linked to a handle driven by the operator. The handle engages a drive gear and rotation thereof is converted to linear reciprocating movement in the driving rack.

Accordingly, it is an object of the present invention to provide an external perfusion pumping apparatus for use in PTCA and other related catheterization procedures which can readily supply a continuous supply of blood or other body fluids at high pumping pressures required for the perfusion of these fluids through catheter minute diameters.

Another object of the present invention is to provide a manually operated pumping apparatus having multiple pump elements supported in a housing, the pumping apparatus including a handle drive assembly operatively engaging the pump elements to simultaneously drive one pumping element in a pumping stroke and another pump element in an aspirating stroke, whereby the pumping apparatus provides a continuous supply of body fluids to a perfusion catheter or other catheter.

Still another object of the present invention is to provide a pumping apparatus for use in perfusion catheterization wherein the pumping apparatus includes two syringe pumps of the type having a plunger component slidable within a barrel component, each of the syringe pumps being supported within a housing such that the barrel components are fixed from movement relative to their plunger components, each of the plunger components engaging an elongated rack member extending longitudinally within the housing, the two pumps being interconnected by way of a pinion gear rotatably mounted in the housing between two rack members and in engagement therewith, the pinion gear driving one of the pumps in a reciprocating manner in response to an opposing, reciprocating movement of the other of the pumps such that at any instant during operation of the pumping apparatus, one of the two syringe pumps is constantly aspirating blood from a blood source and the other of the two syringe pumps is constantly pumping blood from the blood source into the patient to achieve a continuous flow of blood through the apparatus and into the patient at a preselected flowrate to prevent ischemia from occurring in the patient due to a prolonged lack of blood.

Still yet another object of the present invention is to provide an improved pumping apparatus for use in perfusion and other catheterization procedures wherein two syringe pumps are manually powered by a gear-slider mechanism such that each of the two syringe pumps perform alternating pumping and suction strokes, and whereby the gear-slider mechanism returns to each pump to its initial operating position after movement without the necessity for return springs or the like.

These and other objects features an advantages of the present invention will be clearly understood through consideration of the following detailed description.

BRIEF DESCRIPTION OF THE DRAWINGS

In the course of the following detailed description reference will be frequently made to the accompanying drawings in which.

DETAILED DESCRIPTION OF THE PREFERRED EMBODIMENTS

Figure 1:
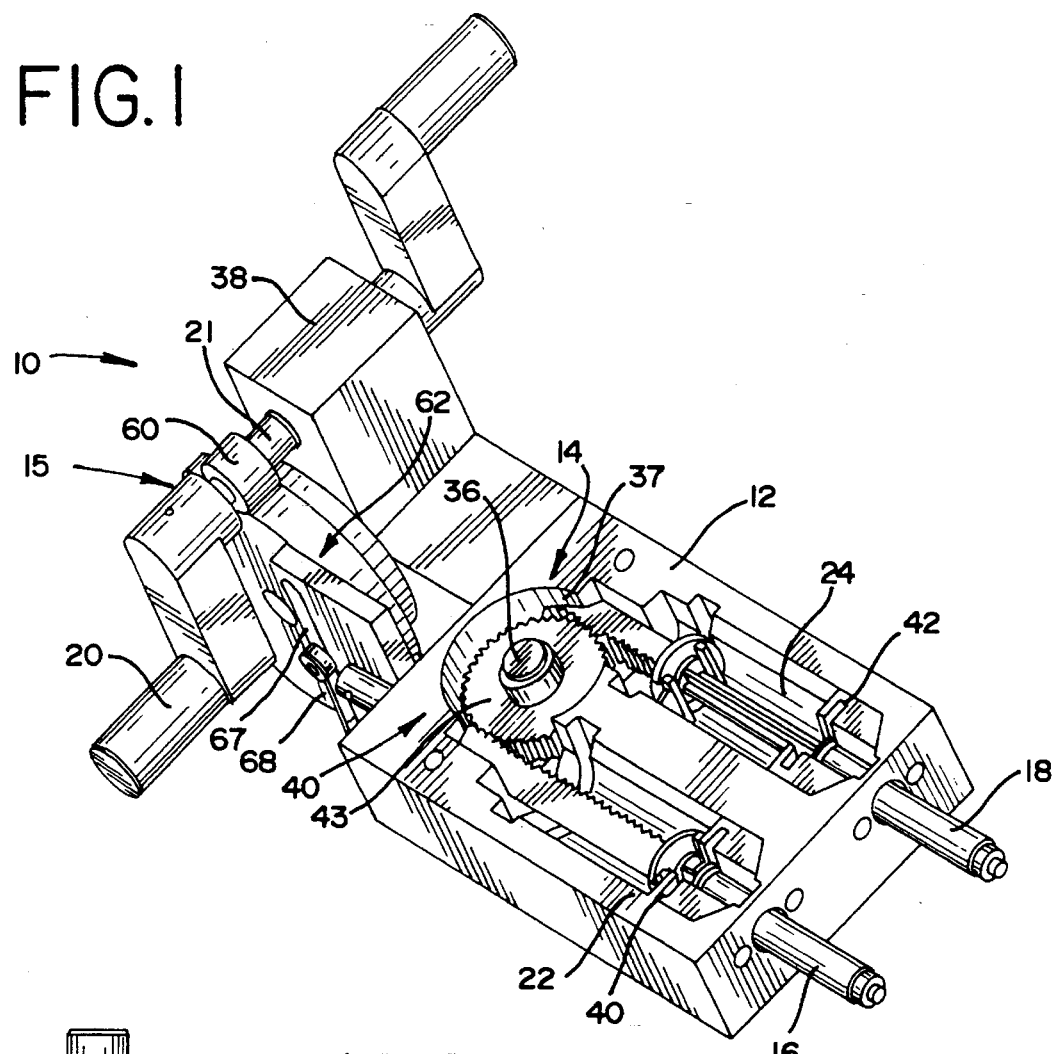
FIG. 1 is a perspective view of a pumping apparatus constructed in accordance with the principles of the present invention.

Referring to the drawings, FIG. 1 illustrates an external pumping apparatus, generally designated as 10, for continuously pumping blood or any other body fluid, into and out of a patient's body during a catheterization procedure, such as PTCA. The apparatus 10 includes a housing portion 12, an actuating assembly 14, a drive assembly 15 and a pair of positive displacement pumps, illustrated as syringe pumps 16, 18. The pumps 16, 18 need not be limited to the syringe pumps shown, but may take the form of any other suitable pumping means so long as one of the pump components may be moved relative to the other pump component. The drive assembly 15 preferably includes a member or assembly for driving the actuating mechanism 14, generally illustrated as a handle 20.

Figure 4:
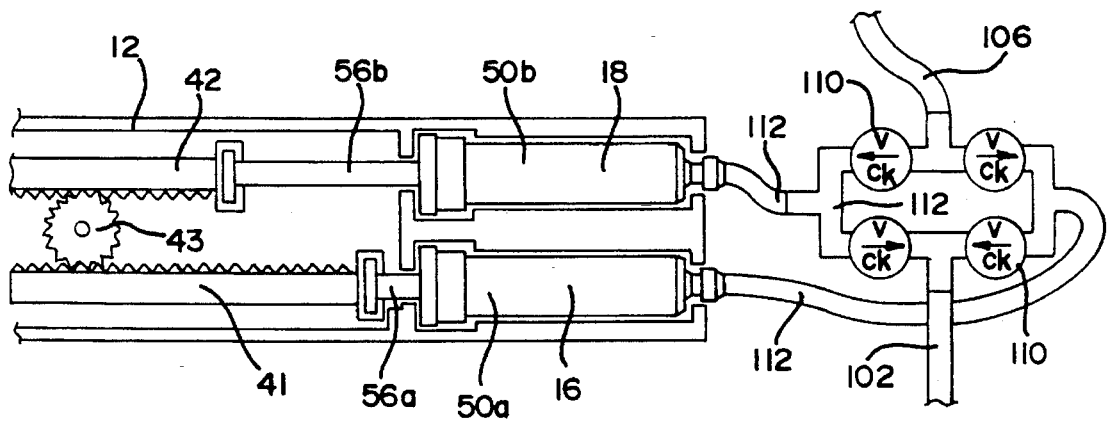

The pumping apparatus 10 of the present invention is particularly useful during catheterization procedures which require continuous perfusion, such as PTCA, wherein a PTCA catheter 102 (FIG. 4) is inserted into an artery of a patient's body and guided to an area of an artery where a blockage, or stenosis has occurred. The PTCA catheter includes an inflatable balloon (not shown) which is inflated when the balloon is located in proximity to the blockage site. During inflation, the balloon is inflated and expanded against the arterial walls and the stenosis in order to exert pressure on the artery and stenosis in order to widen the opening through the blockage. One or more lumens (also not shown) extend through the PTCA catheter and through the balloon. These lumens provide passages for the blood to be perfused into the patient past the blockage to prevent the deficiency of blood and the oxygen it carries to the areas distal of the balloon.

The patient's own blood or body fluids are used in a PTCA or other catheterization procedure by means of an aspiration catheter 106 inserted into a conveniently located artery of the patient. Blood may be drawn through the aspiration catheter 106 by multiple pumps 16, 18 of the pumping apparatus 10. The pumps are coupled together such that, during operation of the handle 20, as one syringe pump 16 operates in a suction stroke to draw blood from the patient's body 104 through the aspiration catheter 106, the other syringe pump 18 operates in a pumping stroke to pump blood previously drawn from the patient's body and back into the patient via PTCA catheter 102.

A suitable flow regulating means, such as an arrangement of check valves 110 and associated tubing 112, is preferably used in association with the present invention, and is illustrated as arranged in-line with the aspiration and PTCA catheters to synchronize and regulate the flow of body fluids into and out of the pumping apparatus 10.

Returning now to FIG. 1, the housing portion 12 supports the two pumps 16, 18 in a manner to fix their respective barrel portions and permit the plunger portions thereof to move within the housing portion 12 during operation. Two channels, or slots, 22, 24 extend longitudinally between opposing end portions 26, 28 of the housing portion 12 which respectively receive the first and second pumps 16, 18 as illustrated. The channels 22, 24 include, at a forward location, means to fix the pump barrel portions within the channels 22, 24, such as slots 40, 42 which engage flanged ends portions 55a, 55b of the pumps and restrain the barrel portions 50a, 50b thereof from movement but permits movement of the pump plunger portions 56a, 56b within the channels 22, 24 and barrel portions 50a, 50b.

The pumps 16, 18 are illustrated as conventional syringe pumps which include elongated cylindrical barrel portions 50a, 50b having outlet openings 52a, 52b disposed at one end and flanged end portions 55a, 55b at the other end thereof. A plunger portion 56a, 56b is received within each respective pump barrel portion 50a, 50b and moves linearly therein in a reciprocating fashion to perform alternating pumping and suction strokes in each pump 16, 18. Pumping chambers 58a, 58b of variable volume are defined in each barrel portion 50a, 50b between the ends 55a, 55b and outlets 52a, 52b of the barrel portions. The volume of each pumping chamber 58a, 58b is maximum where the plunger portions 56a, 56b are located near the rear ends 55a, 55b of the barrel portions and is minimum where they are located near the pump outlet openings 52a, 52b.

In an important aspect of the present invention, the housing 12 accommodates a mechanism 14 for linearly driving the two pumps 16, 18 in a reciprocating manner to simultaneously effect a pumping stroke in one pump and an aspirating stroke in the other pump. This actuating mechanism 14 includes a rack and pinion assembly 40 having a driving rack member 41, a driven rack member 42 and a pinion gear 43. One rack member 41 is operatively connected to one pump plunger member 56a, while the other rack member 42 is connected to the other pump plunger member 56b. The two rack members 41, 42 extend longitudinally within the housing 12 and project into respective housing channels 22, 24. The rack members 41, 42 may be supported in the housing 12 by slots 34, 35 which may include suitable slide bearings (not shown) to provide reduced friction to the rack members 41, 42 during operation.

The pinion gear 43 engages both of the two rack members 41, 42 and is rotatably mounted on a hub 36 located in a recess 37 of the housing between and in communication with both channels 22, 24. The pinion gear 43 includes a plurality of conventional gear teeth 43a formed in its outer perimeter which engage like teeth 41a, 42a formed along the length of each rack member 41, 42. The rack members 41, 42 are oriented in the housing channels 22, 24 so that their respective teeth 41a, 42a face inwardly and opposing each other. In this regard, the two channels 22, 24 intersect the housing recess 37 to permit the rack gear teeth 41a, 42a to extend into the recess 37 along a line of engagement with the pinion gear teeth 43a.

Figure 2A:
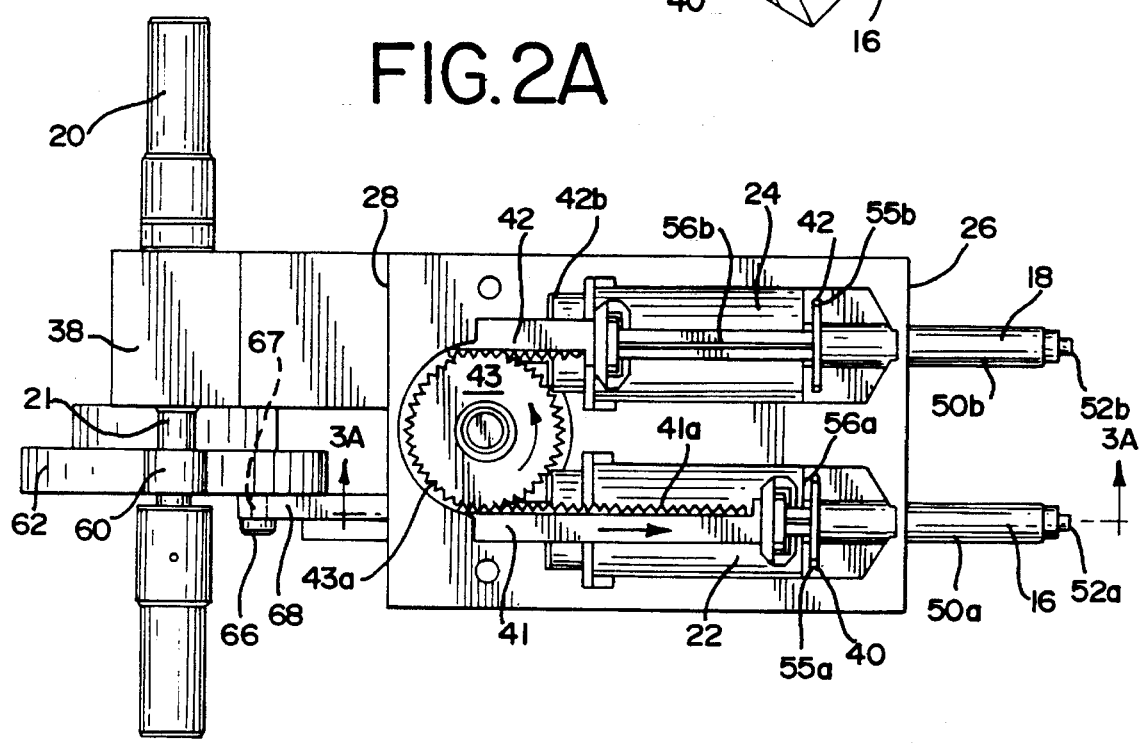
FIG. 2A is a plan view of the pumping apparatus of FIG. 1, generally illustrating a first operating condition of the pumping apparatus.
Figure 2B:
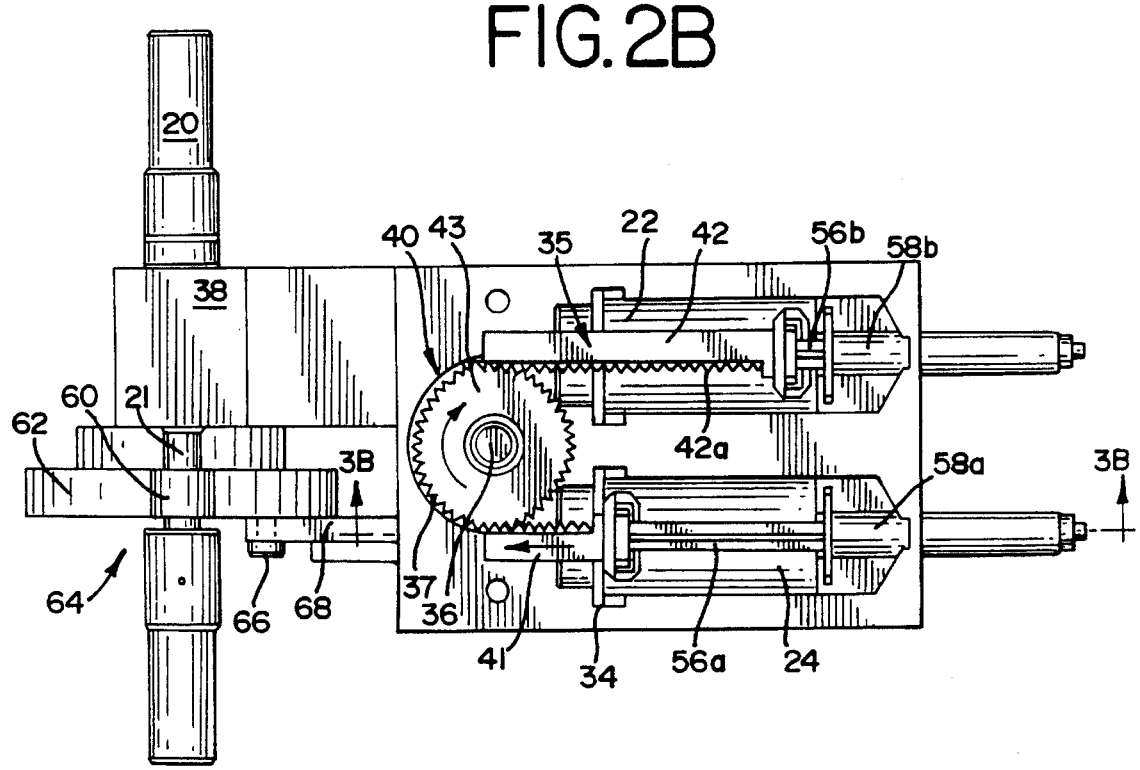
FIG. 2B is the same view as FIG. 2A, but generally illustrating a second operating condition of the pumping apparatus.

As will be seen from a comparison of FIGS. 2A and 2B, the rack and pinion assembly 40 induces two different linear movements in the pumps 16, 18. Rotation of the pinion gear 43 in one direction (shown as counterclockwise in FIG. 2A) moves the rack member 41 forwardly within channel 22, while rack 42 moves rearwardly within channel 24. This movement causes pump 16 to perform a pumping stroke and pump 18 to perform an aspirating stroke. Rotation of the pinion gear 43 in an opposite direction (shown as clockwise in FIG. 2B) causes opposite movements in the two rack members 41, 42, whereby rack member 41 moves rearwardly in channel 22 to cause pump 16 to perform an aspirating stroke, while the other rack member 42 moves forwardly in channel 24 to cause pump 18 to perform a pumping stroke.

In order to operate the pumping apparatus 10 in the manner described above, the pumping apparatus 10 includes a means for driving the two pumps 16, 18, illustrated as an assembly 15 which includes a handle 20. Importantly, the drive assembly 15 converts rotary motion to linear motion. The handle 20 of the drive assembly 15 is rotatably mounted within a support block 38 located rearwardly of and adjacent to the housing 12. The support block 38 preferably supports the handle 20 generally above the top of the housing 12 in order to accommodate the operator's hands and to provide clearance to avoid interference with the other components of the pumping apparatus 10. The handle 20 includes a pinion gear 60 located on its shaft 21. The pinion gear 60 drivingly engages a drive gear 62 rotatably mounted to the support block 38 beneath the handle 20, whereby rotation of the handle 20 causes the pinion gear 60 to rotate and rotate the drive gear 62. The drive gear 62 rotates in a direction opposite that of the direction of rotation of the handle 20. The pinion and drive gears 60, 62 may engage each other by way of gear teeth or by close frictional contact.

The pump actuating mechanism 14 includes a means for engaging the drive assembly 15 and converting the rotary motion thereof to linear motion which reciprocates the two pumps 16, 18 and is illustrated as a slider-crank assembly 64 which includes a drive yoke 68 connected to the driving rack member 41 and which engages the drive gear 62. The engagement between the yoke 68 and drive gear 62 is accomplished by way of a drive pin 66 which is located at a preselected radial distance R from the center of the drive gear 62. As will become apparent below, this radial distance R is chosen to determine the length of the stroke of each syringe pump 16, 18 and is equal to one-half of the stroke. The drive pin 66 extends outwardly from the drive gear 62 and projects through a vertical slot 67 in the drive yoke 68.

Figure 3A:
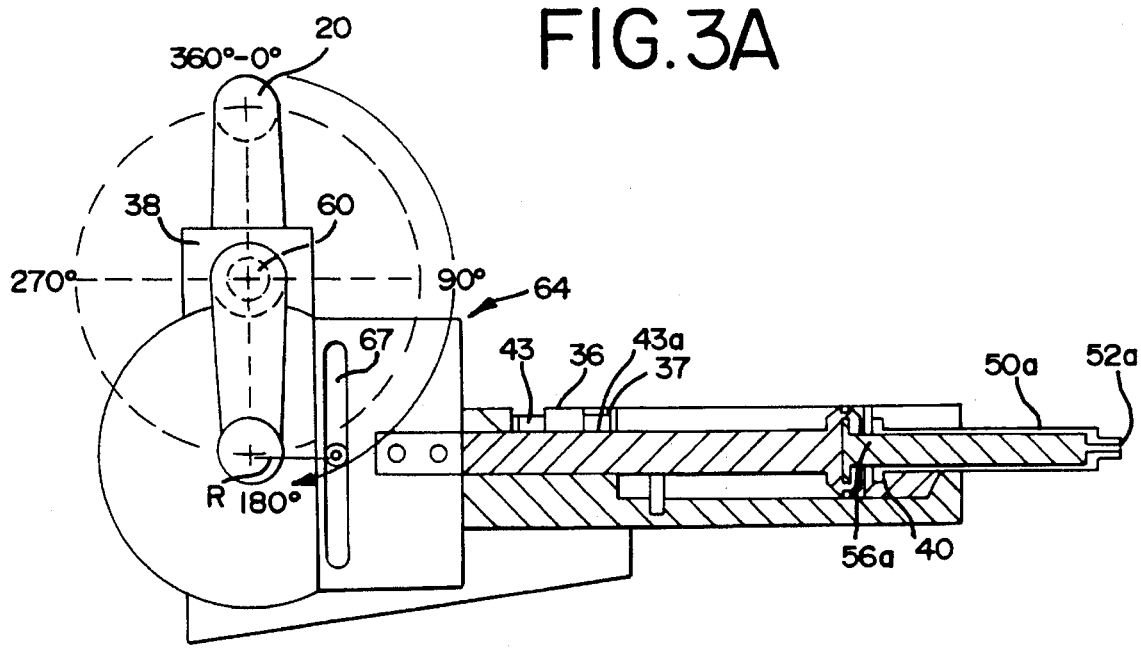
FIG. 3A is an elevational sectional view of the pumping apparatus of FIG. 2A, taken along lines 3A—3A thereof and generally illustrating relative positions between the drive mechanism components and driving rack member in the pumping apparatus first operating condition.
Figure 3B:
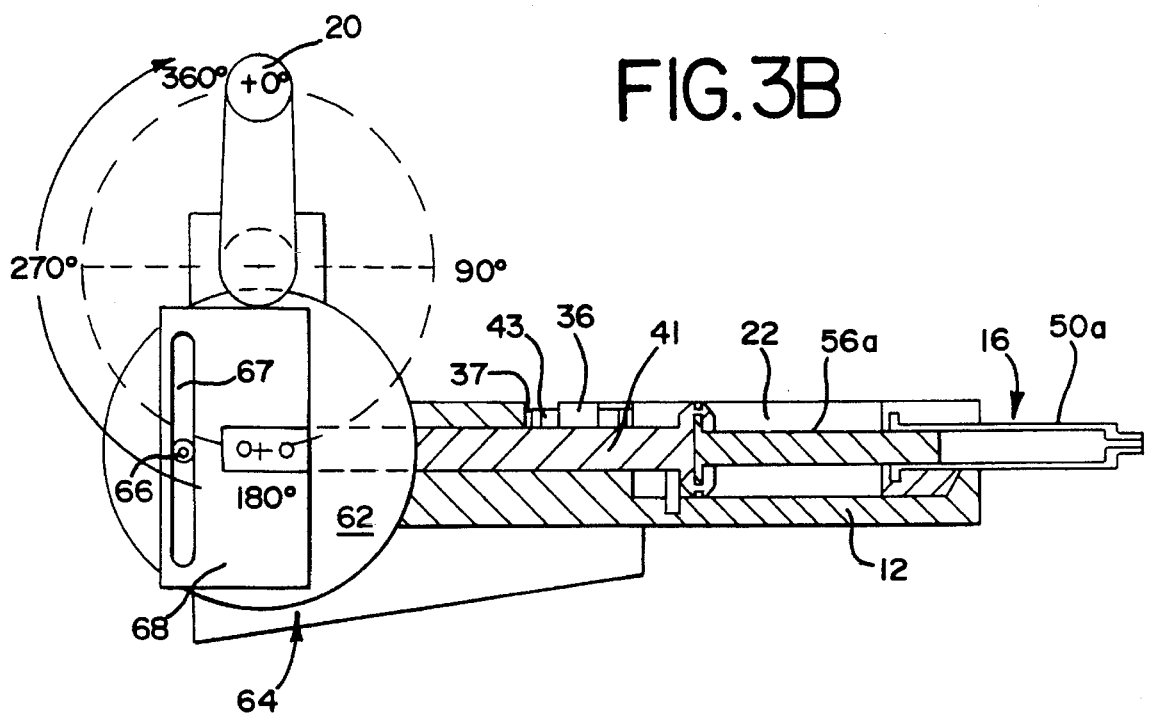
FIG. 3B is an elevational sectional view of the pumping apparatus of FIG. 2B, taken along lines 3B—3B thereof and generally illustrating relative positions between the drive mechanism components and driving rack member in the pumping apparatus second operating condition; and, FIG. 4 is a schematic view of a PTCA system using the pumping apparatus of FIG. 1.

During rotation of the drive gear 62, the drive pin 66 follows a circular path in a direction opposite to the rotation of the handle 20. The drive pin 66 freely moves up and down in the drive yoke slot 67 during rotation without translating any of the rotation of the drive gear 62 to the two rack members 41, 42. However, the slot 67 and its yoke 68 are moved back and forth horizontally between the 0° and 180° reference points illustrated in FIGS. 3A and 3B. Thus, rotary motion of the drive gear 62 is translated to linear movement in the driving rack member 41 which occurs back and forth as shown in FIGS. 3A and 3B. This linear path has a distance of 2R, which is equal to twice the radial distance R of the pin 66 from the center of the drive gear 62.

FIG. 3A is a sectional view which illustrates the pump 16 in a pumping mode, wherein the handle 20 has been rotated from between 0° and 180° and drive gear drive pin 66 occupies its forwardmost position of the drive gear 62. In this position, the plunger 56a of the first pump 16 is displaced forwardly and performs a pumping stroke. The forward movement of the driving rack member 41 causes the pinion gear 43 to rotate counterclockwise which, in turn, drives the driven rack member 42 rearwardly. This rearward movement causes the second pump plunger portion 56b to move rearwardly and perform a suction, or aspirating stroke in the second pump 18. In order to ensure the consistent nature of this reversing drive of the two pumps 16, 18, the pump plunger members 56a, 56b are laterally offset with respect to each other, that is they each engage the rack members 41, 42 at different points within the two channels 22, 24.

Further rotation of the handle 20 from 180° to 360° as illustrated in FIG. 3B causes the drive gear drive pin 66 to adopt a rearmost position. In this position, the yoke 68 is drawn rearwardly as well as the driving rack member 41 affixed thereto. This driving rack member movement causes the pinion gear 43 to rotate clockwise and the driven rack member 42 is moved forwardly and the pump 18 performs a pumping stroke while the first pump 16 performs a suction stroke.

Although the pumping apparatus 10 effectively provides a continuous pumping cycle for the two pumps 16, 18, its operation as a perfusion pumping apparatus is most effective when it is used in conjunction with a fluid flow regulating device (FIG. 4) which includes a plurality of check valves 110 arranged in-line with interconnecting tubing 112. The valves are disposed in the tubing and spaced apart so as to route flow of body fluids from the aspiration catheter 106 to whichever of the two pumps 16, 18 is performing a suction stroke at the time and likewise to route flow of body fluids from whichever pump is performing a pumping stroke to the perfusion catheter 102.

The pumping apparatus of the present inventions is simple and convenient to use. The apparatus can be fabricated inexpensively and the pump elements thereof may be made of inexpensive disposable materials, such as polymers, thereby eliminating any necessity to clean and/or disinfect the apparatus after every use. The present invention therefore provides a pumping apparatus at minimal expense, which can perform the functions of multiple pumps.

While the preferred embodiment of the invention have been shown and described, it will be obvious to those skilled in the art that changes and modifications may be made therein without departing from the spirit of the invention, the scope of which is defined by the appended claims.

We claim:

1. A pumping apparatus for delivering a continuous flow of body fluid to a preselected location within a patient's body, comprising:

first and second pumps, each of the two pumps having a barrel portion defining a pump chamber and a plunger member slidably received within said barrel portion, each of said pump barrel portions having an outlet end for the passage of fluids from the pump chamber out of said pump, a support assembly supporting said first and second pumps such that each of said pump outlet ends is oriented in the same direction and each of said pump barrel portions is restrained from any significant movement with respect to said pump plunger members, the support assembly including first and second channels which respectively receive said first and second pumps and restrain said first and second pumps from movement with respect to said first and second pump plunger members;

an actuating assembly disposed in said support assembly for moving said first and second pump plunger members in a reciprocating manner in and out of said first and second pump barrel portions, said actuating assembly engaging said first and second pump plunger members and supplying linear movement to said first and second pump plunger members, whereby movement of said actuating assembly in a first operating direction causes said actuating member to simultaneously engage said first pump in a suction stroke and said second pump in a pumping stroke and, whereby movement of said actuating assembly in a second operating direction, opposite to said first direction, causes said actuating assembly to simultaneously engage said first pump in a pumping stroke and said second pump in a suction stroke; and, a rotatable drive assembly which drives said actuating assembly, the drive assembly including means for converting rotational motion of said drive assembly into linear motion which drives said actuating assembly between said first and second operating directions.

2. The pumping apparatus of claim 1, wherein said first and second pumps are syringe pumps.

3. The pumping apparatus of claim 1, wherein said actuating assembly includes a rack and pinion assembly having first and second rack members operatively engaging said respective first and second pumps, the first rack member being a driving rack member operatively engaging said drive assembly and the second rack member being a driven rack member operatively engaging said driving rack member.

4. The pumping apparatus of claim 3, wherein each of said rack members are supported within said support assembly in alignment with said first and second pump plunger members and said rack and pinion assembly further including a pinion gear rotatably supported in said housing between said two rack members and in driving engagement therewith.

5. The pumping apparatus of claim 1, wherein said support assembly first and second channels each include a slot portion which engages said respective first and second pump barrel portions to restrain said first and second pump barrel portions from movement within said first and second channels with respect to said first and second pump plunger members.

6. The pumping apparatus of claim 5, wherein said drive assembly includes a handle rotatably mounted on said support assembly, a drive gear drivingly engaging the handle and a yoke member, the yoke member engaging said first rack member.

7. The pumping apparatus of claim 1, wherein said drive assembly includes a handle adapted for rotation on said support assembly and a drive gear driven by said handle, said motion converting means including a yoke member operatively engaging said drive gear, said yoke including a slot portion therein and said drive gear including a projection member which engages said slot portion, whereby rotation of said drive gear reciprocates said yoke member back and forth along a linear path.

8. The pumping apparatus of claim 7, wherein said yoke member operatively engages said first rack member.

9. The pumping apparatus of claim 7, wherein said handle frictionally engages said drive gear.

10. The pumping apparatus of claim 7, wherein each of said first and second pump plunger members have a stroke within their respective pump chambers which are twice the radial distance between said projection member and a center of said drive gear.

11. The pumping apparatus of claim 7 wherein said handle includes a pinion gear which drivingly engages said drive gear.

12. The pumping apparatus of claim 1, further including a rack and pinion assembly and first and second channels disposed within said support assembly between a recess accommodating a pinion gear of said rack and pinion assembly, said first and second channels opening into said recess, said pumping apparatus further including first and second rack members slidably disposed in said first and second channels, the first and second rack members engaging said pinion gear, whereby movement one of said first and second rack members induces an opposite movement in said other rack member in a direction opposite that of said one rack member, said first and second pump plunger members engaging said first and second rack members in a manner wherein one of said first and second pump plunger members is laterally offset within said support assembly with respect to an other of said first and second pump plunger members.

13. The pumping apparatus of claim 1, wherein said motion converting means includes a slider crank mechanism.

14. A pumping apparatus for pumping blood comprising:
a housing, including two channels,
first and second pumps disposed on the housing, each of the two pumps having an elongated barrel defining a pump chamber therein and further having a plunger slidably received within said pump chamber, each of the two channels respectively accommodating said plungers and barrels of said first and second pumps, said first and second channels further restraining said first and second pump barrels from movement with respect to said first and second pump plungers;
an actuating assembly for simultaneously actuating each of said first and second plungers of said first and second pumps in opposite directions; and,
a driving assembly for driving said actuating assembly, the actuating assembly including first and second rack members operatively engaging said first and second pumps, said actuating assembly further including a pinion gear for driving said rack members in said opposite directions between two operative positions, said pinion gear operatively engaging said first and second rack members, whereby movement of said pinion gear in a first direction in response to movement of said drive assembly effects a pumping stroke in said first pump and an intake stroke in said second pump, and whereby movement of said pinion gear in a second direction in response movement of said drive assembly effects an intake stroke in said first pump and a pumping stroke in said second pump, said drive assembly further including a handle driving a drive gear which engages the handle and which also engages one of said rack members, said drive gear including a connection member extending therefrom and engaging a yoke member extending from said one rack member, whereby rotation of said drive gear causes said pin member to move the yoke member to reciprocate along a linear path, said connection member thereby converting rotation of said handle into linear movement of said yoke member which is transferred to said one rack member, said pinion gear causing said other rack member to move in a direction opposite that of said one rack member.

15. The pumping apparatus of claim 14, wherein said housing includes two openings disposed in an end portion thereof and in general alignment with said two channels, each of said openings receiving said pump barrel portions.

16. The pumping apparatus of claim 14, wherein each of said two channels includes means for restraining said first and second pump barrel portions from movement with respect to said plungers.

17. The pumping apparatus of claim 14, wherein each of said pumps are syringe pumps.

18. The pumping apparatus of claim 17, wherein said syringe pumps are disposed on said housing generally parallel to each other.

19. The pumping apparatus of claim 14, wherein said one rack member engages said yoke member and further is a driving rack member and said other of said rack members is a driven rack member, said driving rack member receiving drive from said drive assembly, and said driven rack member receiving drive from said pinion gear.

20. A pumping apparatus for pumping blood comprising:
first and second syringe pumps, each of the syringe pumps having a barrel portion defining a pump chamber therein and said pumps further having a plunger member slidably received within said pump chamber;
a base supporting said first and second syringe pumps, said base fixedly engaging said first and second syringe pump barrel portions with respect to said first and second pump plunger members by way of first and second channels by which said first and second syringe pumps are engaged by said base;
an actuating assembly for simultaneously moving each of said first and second pumps in alternating pumping and suction strokes, the actuating assembly including a pinion gear and two elongated rack members operatively connected to said pump plunger members, the pinion gear being disposed on said base between the two rack members and reciprocatingly driving each of said rack members in opposite directions between two operative positions, said pinion gear being driven by movement of said first rack member and said pinion gear consequently driving said second rack member in a direction opposite said first rack member;
a drive assembly for supplying drive to said actuating assembly, said drive assembly including a rotatable handle, the handle engaging a drive gear, the drive assembly further including a yoke transversely disposed with respect to said pinion gear and operatively connecting said drive gear with said first rack member, said yoke including a linear opening which receives a post member extending from said drive gear, whereby, the engagement between said drive gear post member and yoke opening converts rotational movement of said handle which is imparted to said drive gear into reciprocating linear movement of said first rack member, whereby movement of said handle through 180° of rotation causes said pinion gear to drive said first syringe pump in a suction stroke and to simultaneously engage said second syringe pump in a pumping stroke, and whereby movement of said handle through an additional 180° of rotation causes said pinion gear to drive said first pump in a pumping stroke and to engage said second syringe pump in a suction stroke.

* * * * *